(12) United States Patent
Merkus

(10) Patent No.: US 11,813,353 B2
(45) Date of Patent: Nov. 14, 2023

(54) PHARMACEUTICAL COMPOSITIONS FOR THE NASAL ADMINISTRATION OF A COBALAMIN COMPOUND

(71) Applicant: INNOTESTO BV, Kasterlee (BE)

(72) Inventor: Franciscus Merkus, Kasterlee (BE)

(73) Assignee: INNOTESTO BV, Kasterlee (BE)

( * ) Notice: Subject to any disclaimer, the term of this patent is extended or adjusted under 35 U.S.C. 154(b) by 0 days.

(21) Appl. No.: 18/007,003

(22) PCT Filed: Aug. 27, 2021

(86) PCT No.: PCT/EP2021/073796
§ 371 (c)(1),
(2) Date: Jan. 26, 2023

(87) PCT Pub. No.: WO2022/043526
PCT Pub. Date: Mar. 3, 2022

(65) Prior Publication Data
US 2023/0210766 A1 Jul. 6, 2023

(30) Foreign Application Priority Data
Aug. 31, 2020 (GB) .................................... 2013645

(51) Int. Cl.
| | | |
|---|---|---|
| A61K 9/00 | (2006.01) |
| A61K 31/714 | (2006.01) |
| A61K 47/12 | (2006.01) |
| A61K 47/26 | (2006.01) |
| A61K 9/08 | (2006.01) |

(52) U.S. Cl.
CPC .......... *A61K 9/0043* (2013.01); *A61K 31/714* (2013.01); *A61K 47/12* (2013.01); *A61K 47/26* (2013.01); *A61K 9/08* (2013.01)

(58) Field of Classification Search
None
See application file for complete search history.

(56) References Cited

U.S. PATENT DOCUMENTS

| | | |
|---|---|---|
| 4,724,231 A | 2/1988 | Wenig |
| 5,801,161 A | 9/1998 | Merkus |
| 5,925,625 A | 7/1999 | Merkus |
| 6,379,688 B2 * | 4/2002 | Yamaguchi ............ A61K 47/02 514/939 |
| 2008/0039422 A1 * | 2/2008 | Cruz .................... A61K 9/0019 514/52 |

FOREIGN PATENT DOCUMENTS

| | | | |
|---|---|---|---|
| EP | 0735859 | * | 5/1994 |
| WO | 2007050272 A2 | | 5/2007 |
| WO | 2012056299 A1 | | 5/2012 |
| WO | 2022043526 A1 | | 3/2022 |

OTHER PUBLICATIONS

Hofmann et al. "Influence of Preservatives and Topical Steroids on Ciliary Beat Frequency In Vitro", Arch Otolaryngol Head Neck Surg/vol. 130, Apr. 2004, pp. 440-445.
Horvath et al. "Cytotoxicity of Different Excipients on RPMI 2650 Human Nasal Epithelial Cells" Molecules 2016, 21, 658, 5 pgs.
International Preliminary Report on Patentability dated Jan. 26, 2022, pertaining to Int'l Patent Application No. PCT/EP2021/073796, 7 pgs.
International Search Report and Written Opinion dated Dec. 3, 2021, pertaining to Int'l Patent Application No. PCT/EP2021/073796, 14 pgs.
Kang et al. "Vitamin B12 modulates the transcriptome of the skin microbiota in acne pathogenesis", www.ScienceTranslationalMedicine.org, Jun. 24, 2015, vol. 7 Issue 293, pp. 1-12.
Rowe et al. Handbook of Pharmaceutical Excipients, 7th edn. London: Pharmaceutical Press, 2012, pp. 479-482.
Van Asselt et al. "Nasal absorption of hydroxocobalamin in healthy elderly adults", Br J Clin Pharmacol 1998; 45: 83-86.
Slot et al. "Normalization of Plasma Vitamin B12 Concentration by Intranasal Hydroxocobalamin in Vitamin B12-Deficient Patients", Gastroenterology 1997; 113: 430-433.
Okhosrt et al. "Side effect mainly affects women Acne-like bumps due to vitamin B12", Pharmaceutisch Weekblad , Apr. 5, 2013, 16-17.
Martindale "Vitamin B12 Substances", The Complete Drug Reference, 35th Edition, S. Sweetman, Pharmaceutical Press, 2007, p. 1817.

* cited by examiner

Primary Examiner — Melissa S Mercier
(74) Attorney, Agent, or Firm — DINSMORE & SHOHL, LLP

(57) ABSTRACT

The invention relates to a pharmaceutical formulation, in a composition and form suitable for intranasal administration as a spray or drops or gel, containing hydroxocobalamin and/or hydroxocobalamin salts dissolved in water, containing mannitol as main excipient and optionally some other excipients.

5 Claims, No Drawings

PHARMACEUTICAL COMPOSITIONS FOR THE NASAL ADMINISTRATION OF A COBALAMIN COMPOUND

CROSS REFERENCES TO RELATED APPLICATIONS

This application is a national-stage application under 35 U.S.C. § 371 of International Application No. PCT/EP2021/073796, filed Aug. 27, 2021, which International Application claims benefit of priority to Great British Patent Application No. 2013645.3, filed Aug. 31, 2020.

The present invention relates to intranasal compositions of hydroxocobalamin (and/or its salts) and the process of the preparation of such intranasal compositions.

BACKGROUND OF THE INVENTION

Hydroxocobalamin is a natural form of vitamin B12. It is a member of the cobalamin family of compounds. Vitamin B 12 is an essential vitamin, necessary for the formation of blood cells, the nervous system and the production of important proteins. Animal products (eggs, meat, milk etc.) are the only source of vitamin B12 in the human diet. Vitamin B12 deficiency happens when the digestive system is not able to absorb the vitamin. This occurs in people with pernicious anemia (in this anemia, the mechanism to absorb vitamin B12 by the so-called intrinsic factor is absent), and also in patients after gastric or bowel surgery, in veganists and vegetarians and in patients with sprue (also called celiac disease), Crohn's disease, pancreas insufficiency, AIDS and alcoholics.

A large part of the elderly population has a vitamin B12 deficiency, causing hematological and neurological disorders. Also vitamin B12 deficiency has been associated with an increased risk for Alzheimer disease and reduced cognitive function. It is also frequently mentioned as a comorbidity in Parkinson's disease. Methylcobalamin has been reported to be effective in a variety of patients with neurological symptoms and behavioural disturbances, like ADHD and autism.

Vitamin B12 is used as an injection. Oral vitamin B 12 tablets are widely available in health shops, but the oral bioavailability is negligible in patients with a vitamin B12 deficient absorption.

Vitamin B12 occurs in the human body as hydroxocobalamin, methylcobalamin, and adenosylcobalamin. The first product that was made synthetically is cyanocobalamin (it contains cyanide). For historical reasons, the main form used therapeutically in the USA is cyanocobalamin. In many other countries (e.g. in Europe) hydroxocobalamin is the drug of choice, and it is the preferred compound for instance by modern pharmacology textbooks and by the WHO Model List of Essential Medicines.

Hydroxocobalamin is longer acting than cyanocobalamin, because it has a longer elimination half-life in the human body. It is more extensively bound to plasma proteins. Secondly, hydroxocobalamin does not contain CN (cyanide). Cyanocobalamin is therefore contraindicated in people with relatively high CN-levels (in tobacco and tropical amblyopia, and in optic neuropathy). Methylcobalamin is not widely available in the world, and is not the drug of choice in pharmacopoeias and textbooks.

Vitamin B12 status is typically assessed via serum or plasma vitamin B12 levels. Normal levels are between about 200-900 pg/ml. Values of less than 200 pg/ml are considered a sign of a vitamin B12 deficiency. Older adults with vitamin B12 levels between 200 and 500 pg/mL may also show symptoms of B12 deficiency. Values are usually expressed in pg/ml (=ng/l) (vitamin B12 conversion factor: 1 pg/ml=0.738 pmol/l, and 1 pmol/l=1.355 pg/ml).

Medical standard therapy is a monthly intramuscular injection of vitamin B12, which has to be continued for life. These intramuscular injections have serious disadvantages. In the first place, because they are inconvenient and painful and secondly, they need the assistance of health professionals which makes the whole therapy very expensive. A substantial need exists for a more patient-friendly and more cost-effective therapy. For that reason nasal application has been developed.

U.S. Pat. No. 4,724,231 teaches a therapeutic composition for nasal administration comprising a vitamin B12, an isotonic aqueous buffer to provide a pH of from about 4 to 6 and a thickening agent so that the viscosity of the composition is from about 2500 to 10,000 Cps. The pH of the compositions of this invention is from about 4 to 6. The pH is maintained with a buffer composition suitably an acetate, citrate, phosphate, phthalate, borate, or other buffer. Acetate and citrate buffers are preferred for convenience and economy. The isotonicity of the composition is accomplished by adding sodium chloride, or other pharmaceutically acceptable agents such as dextrose, boric acid, sodium tartrate or other inorganic or organic excipients. Sodium chloride is preferred particularly for buffers containing sodium ions. Viscosity of the compositions is maintained with methyl cellulose or with xanthan gum, carboxymethyl cellulose, hydroxypropyl cellulose, carbomer, and the like. Preferred compositions of U.S. Pat. No. 4,724,231 contain a humectant, for example sorbitol, propylene glycol or glycerol, to inhibit drying of the mucous membrane and to prevent irritation. The concentration will vary with the selected agent. The "presence or absence of these agents, or their concentration is not an essential feature" (column 3, lines 15-17) in U.S. Pat. No. 4,724,231.

U.S. Pat. No. 5,801,161 teaches that for hydroxocobalamin to be absorbed intranasally in high amounts the concentration must be greater than 1% (w/v).

U.S. Pat. No. 5,925,625 teaches that the nasal absorption efficiency of hydroxocobalamin increases with the increasing concentration of hydroxocobalamin in the nasal formulation and that therefore the total concentration of hydroxocobalamin to be absorbed nasally in the treatment or prophylaxis of vascular headache must be in the range of 1.1-10% (w/w). In U.S. Pat. No. 5,925,625 no reference is made to the use of mannitol as an excipient in nasal hydroxocobalamin compositions.

U.S. Pat. No. 7,229,636 discloses low viscosity aqueous formulations of cyanocobalamin for intranasal delivery having a pH 4-6 and addresses the problems of the highly viscous intranasal gel and provides a more acceptable low viscous intranasal cyanocobalamin intranasal formulation.

US 2008/039422 discloses solutions of vitamin B12 compounds for injection purposes (i.m., i.v. and s.c.) in a concentration of at least 20 mg/ml (2% w/v). containing "at least one alcohol". These alcohols can be "ethanol, propylene glycol, a polyethylene glycol, a glycerol, sorbitol, mannitol or a combination thereof".

However, sorbitol and mannitol, also called sugar alcohols, are white powders and not known as effective solvents. More importantly, in the present invention composition, the alcohols mentioned in US 2006/039422 are not needed to solubilize hydroxocobalamin, because (in contrast to cyanocobalamin) hydroxocobalamin as sulfate, as acetate and as hydrochloride, is soluble in water up to 1:10 w/w (source:

Martindale: The Complete Drug Reference 35$^{th}$ Edition, S. Sweetman, Pharmaceutical Press, 2007, page 1817 Vitamin B12 substances).

WO2012/056299 discloses intranasal aqueous compositions comprising methylcobalamin or cyanocobalamin in concentration from 500 mcg/0.1 ml to 1500 mcg/0.1 ml, co-solvents/solubilisers or mixtures thereof in water, and in particular with penetration enhancers to enhance the nasal absorption, and optionally preservatives, mucoadhesive agents, chelating agents, humectants, antioxidants, or combinations thereof, and wherein the pH of the composition is 5 to 7 and viscosity of 1 to 200 Cps.

A large variety of auxiliary substances have been proposed in the literature to be used in nasal drug formulations for systemic drug delivery. In a study on the cytotoxicity of several excipients on nasal epithelial cells, the investigators concluded that mannitol in a 1% concentration caused no cellular damage, and in the conclusion of their study mannitol 0.3% is "suggested to be used in nasal vehicles" (Horvath T. et al. Molecules 2016, 21, 658).

Vitamin B12 therapy, especially the injection therapy is linked to a remarkable effect Injections are causing unphysiologically high cobalamin blood level, with extreme high levels of between 20 000 and 30 000 pg/ml and at the same time after injection of cobalamines exacerbation or onset of inflammatory acne and folliculitis have been reported. The mechanisms of vitamin B12-induced acne have been described by Kang et al (Science Translational Medicine 2015, vol 7, issue 293, 293ra103).

When present, acneiform eruptions usually occur on the facial area after the first or second injection, and typically disappear within 8 to 10 days after stopping therapy. In the Netherlands about 45 incidences of acneiform dermatitis after vitamin B12 injections (mainly hydroxocobalamin) have been described (B. Lokhorst and K. Grootheest, Pharmaceutisch Weekblad, 5 Apr. 2013, 16-17). Also drug information concerning the high dose hydroxocobalamin injection (Cyanokit®) teaches that the patient may develop an acne like skin rash within 1-4 weeks.

Since, acneiform eruptions usually occur after the first or second injection and disappear when the injection therapy is stopped, there is obviously a relation between the high blood levels and the onset of the inflammatory acne. Therefore, there is a need for a vitamin B12 therapy avoiding high blood levels, which are concomitant with injection therapy.

Patients preferably need a vitamin B12 supplementation therapy resulting in physiological blood levels between 200-900 pg/ml, and not exceeding maximum levels of about 2000 pg/ml, preferably not exceeding 1500 pg/ml. The question is whether nasal hydroxocobalamin therapy could be offering such a therapy.

In the USA two cyanocobalamin nasal products have been developed (Nascobal®, Calomist®). Nascobal is a solution of Cyanocobalamin, USP (vitamin B12) for administration as a spray to the nasal mucosa. Each unit dose nasal spray of Nascobal delivers 500 mcg/0.1 mL solution of cyanocobalamin with sodium citrate, citric acid, glycerin and the preservative benzalkonium chloride in purified water. The spray solution has a pH between 4.5 and 5.5. The recommended dose is 500 mcg/0.1 ml in one nostril per week. The other product is Calomist, a solution of cyanocobalamin for administration as a metered spray to the nasal mucosa. Each bottle contains 10.7 mL of a 25 mcg/0.1 mL solution of cyanocobalamin. The spray solution has a pH between 6.5 and 7.5. It further contains sodium chloride, sodium phosphate monobasic, the preservative benzyl alcohol, sodium hydroxide, and the preservative benzalkonium chloride in purified water with an attached spray pump unit The recommended initial dose is one spray in each nostril once daily (25 mcg per nostril, total daily dose 50 mcg). The dose should be increased to one spray in each nostril twice daily (total daily dose 100 mcg) for patients with an inadequate response to once daily dosing. Both products Nascobal and Calomist contain cyanocobalamin, which for reasons explained above is not the best physiological vitamin B12 compound. Secondly these nasal products contain as preservative benzalkonium chloride which has a negative effect on the normal mucociliary clearance in the nose.

Several studies investigating a hydroxocobalamin nasal spray has been described in the literature. In one study with 6 Crohn's disease patients received on three different days 1500 µg nasal hydroxocobalamin (Bruins Slot W et al. Gastroenterology 1997;113:430-433). The increase in vitamin B12 level (in pg/ml) on day 0, day 14, day 21 was: in Patient A: 900, 810, 2080; Patient B: 520, 520, 530; Patient C: 1340, 2260, 2080; Patient D: 2230, 2030, 1850; Patient E: 2320, 1880, 1860; Patient F: 1580, 1040, 1530. This is a mean increase of 1520 pg/ml (SD 645 pg/ml, or CV=42.5% expressed as coefficient of variation (CV).

In a second study in 10 geriatric patients the mean Cmax levels after doses of 750 µg and after 1500 µg were rather high in some cases and, more importantly, the interindividual variation was large. The Cmax levels (±SD) after nasal administration were 2700±1200 pg/ml (after a dose of 750 µg) and 4700±3400 pg/ml (after a dose of 1500 mg). The SD of both Cmax levels, expressed as CV (coefficient of variation), was 44%, after a dose of 750 µg, and 72%, after a dose of 1500 mg (Van Asselt D. et al, Br. J. Clin. Pharmacol. 1998; 45: 83-86).

The Standard Deviations of the obtained Cmax levels in these nasal hydroxocobalamin studies, expressed as coefficients of variation, 72%, 44% and 42.5, are large. This demonstrates a variable, not consistent, nasal absorption process. Therefore there is a need for a nasal hydroxocobalamin therapy providing a much more consistent absorption and a smaller coefficient of variation and with Cmax levels not exceeding 2000 pg/ml, preferably not exceeding 1500 pg/ml. In other words a nasal hydroxocobalamin product causing a maximal increase of the cobalamin level of about 500-1000 pg/ml per dose given, whereby the mean Cmax does not exceed a maximum of about 2000 pg/ml, preferably not exceeding 1500 pg/ml and offering a mean maximal increase in vitamin B12 levels with a coefficient of variation smaller than 72%, smaller than 44%, and smaller than 42.5%.

Cobalamin vitamins have all a intense dark red color. After regular nasal delivery of a cyanocobalamin or hydroxocobalamin spray, the interaction of the cobalamin compound with its intense color and the mucus in the nose, may cause dark red crusts (crustae) in the nose, suggesting the presence of blood in the nose. Also hours after administering nasal cobalamin a paper tissue or handkerchief to clean the nose, will color red, suggesting a nose bleeding. It shows, that the mucociliary clearance of the red colored non absorbed cobalamin did not function properly. There is therefore a need for a nasal therapy providing a nasal composition which is cleared fast from the nose either by absorption or by the normal mucociliary clearance.

A large part of the nasal products currently on the market (including Nascobal and Calomist) contain benzalkonium chloride as a preservative. Calomist contains benzyl alcohol as a second preservative. From the literature it is known that these preservatives may strongly reduce the nasal ciliary beat frequency with as a consequence a severe reduction of the normal nasal mucociliary clearance. Therefore there is a need for a nasal vitamin B12 therapy without the use of these preservatives.

OBJECTS OF THE INVENTION

The main object of the invention is to provide an improved nasal dosage form to administer hydroxocobalamin by the nasal route in a specific composition.

It is an object of the invention to provide an aqueous nasal hydroxocobalamin solution to be administered as a nasal spray or drops or nasal gel from which the cobalamin compound is absorbed quickly and consistently into the bloodstream via the mucosal membranes in the nasal cavity, and to provide methods to manufacture such a product and to provide a method and/or a device to administer such an nasal product.

It is an object of the invention to provide a nasal hydroxocobalamin solution to be administered as a nasal spray or drops or nasal gel causing preferably a maximal increase of the cobalamin level (Cmax) of about 500-1000 pg/ml per dose given.

It is an another object of the invention to provide a nasal hydroxocobalamin solution to be administered as a nasal spray or drops or nasal gel, whereby the Cmax does not exceed a maximum of about 2000 pg/ml, preferably about 1500 pg/ml. Also, there is a need for a nasal product offering a mean maximal vitamin B12 levels with a coefficient of variation smaller than 72%, smaller than 44%, and smaller than 42.5%.

It is a further object of the invention to provide a nasal hydroxocobalamin solution to be administered as a nasal spray or drops or nasal gel with a composition not containing preservatives like benzalkonium chloride and/or benzyl alcohol.

It is another object of the invention to provide a nasal hydroxocobalamin solution to be administered as a nasal spray or drops or nasal gel using compositions with the use of a safe preservative.

A further object of the invention is to provide an aqueous hydroxocobalamin composition for nasal administration containing optionally one or more solvents, selected from glycerol, propylene glycol, polyethylene glycol, alkoxypolyethylene glycol and one or more other excipients, selected from buffers to keep the pH between 4-8, antioxidants, agents to adjust the pH, surfactants, complexing agents, stabilizers and solubilizers.

DESCRIPTION OF THE INVENTION

The present invention composition provides an aqueous formulation for intranasal administration containing as active drug hydroxocobalamin and/or one of its pharmaceutically acceptable salts, such as hydroxocobalamin chloride, sulfate and acetate and similar derivatives Cobalamin compounds are large hydrophilic molecules (about 1350 Dalton) and their transport across nasal epithelial membranes is paracellular. Such a transport may be favoured by an excipient in the nasal formulation which opens tight junctions between nasal epithelial cells.

We have surprisingly found that inclusion of mannitol in the nasal composition, in a concentration of between 3%-12% mannitol (w/v), preferably between 5%-10% (w/v), favours a consistent absorption of the cobalamin compound. Mannitol 5% is iso-osmotic with serum (Rowe et al, eds, Handbook of Pharmaceutical Excipients, 7$^{th}$ Edn, London: Pharmaceutical Press, 2012). Higher levels than mannitol 5% (w/v) are hyperosmotic.

Surprisingly, mannitol in the present invention composition is a very efficient facilitating agent for the nasal absorption of hydroxocobalamin. The hydrophilic molecule hydroxocobalamin with a molecular weight of about 1350 can pass epithelial membranes only via the paracellular route, this means only through gaps between the cells. A hyperosmotic concentration of mannitol in the invention formulation causes the composition to be hyperosmotic to the nasal epithelial cells. In order to create an osmotic equilibrium, water leaves the nasal epithelial cells, improves the fluidity of the mucus layer in the nose, and causes the nasal epithelial cells to shrink, at the same time stretching the tight junctions between the cells. Stretching means that newly formed gaps stay open for a short period of time enabling diffusion of hydroxocobalamin through the gaps between nasal cells into the systemic blood circulation. Surprisingly, this makes mannitol an indispensable agent to facilitate a consistent nasal absorption of hydroxocobalamin.

In the present invention compositions, mannitol is not only providing the consistent absorption of hydroxocobalamin, but it increases the fluidity of the nasal mucus supporting and also restoring the normal mucociliary clearance. This may reduce or prevent the forming of red crustae. These features make surprisingly mannitol as the preferred excipient to facilitate an effective nasal absorption of hydroxocobalamin.

The present invention provides novel formulations of hydroxocobalamin (and/or one of its pharmaceutically acceptable salts) for nasal administration, containing mannitol and water as the main excipients, with an optimized absorption profile in order to achieve a rise of the cobalamin blood levels to maximal levels not exceeding 2000 pg/ml, preferably not exceeding 1500 pg/ml. With such compositions it is possible to achieve physiological maximal blood levels and at the same time avoiding very high blood levels and the inherent risk of acneiform dermatitis, providing also a consistent absorption (small variation in absorption), and offering also reduction in side effects such as less red crustae and a quick return to normal nasal mucociliary clearance.

The present invention provides a composition for nasal administration comprising hydroxocobalamin (and/or one of its pharmaceutically acceptable salts) in a concentration above 0.1% (w/v) dissolved in water and containing 3%-12% mannitol, preferably between 5-10% mannitol (all w/v).

The embodiments of the present invention provide compositions for nasal administration comprising hydroxocobalamin and/or any other pharmaceutically acceptable hydroxocobalamin salt, dissolved in a concentration above 0.1% (w/v) in water containing for instance 0.5%, or 1%, or 1.5% (w/v) hydroxocobalamin (as hydroxocobalamin or one of its salts) and optionally one or more pharmaceutical excipients.

In a further embodiments, the present invention provides a composition for nasal administration comprising hydroxocobalamin and/or any other pharmaceutically acceptable salt, dissolved in a concentration between 0.1% (w/v) and 2% (w/v) in water containing at least 3% (w/v) of mannitol and less than about 12% mannitol (w/v), and containing optionally one or more solvents, selected from glycerol, propylene glycol, polyethylene glycol, alkoxypolyethylene glycol and one or more other excipients, selected from buffers, antioxidants, agents to adjust the pH, surfactants, complexing agents, stabilizers and solubilizers.

We have surprisingly found that propylene glycol is an important excipient in the current invention formulation. Propylene glycol is iso-osmotic with serum in a concentration of 2% (Rowe et al, eds, Handbook of Pharmaceutical Excipients, 7th Edn, London: Pharmaceutical Press, 2012). Higher concentrations of propylene glycol are hyperosmotic and they are increasing the 'hyperosmotic effect' of the invention formulation containing mannitol.

Suitably, the composition of the present disclosure may comprise 3%, 4%, 5%, 6%, 7%, 8%, 9% 10%, 11%, 12%, 13%,14% and 15% v/v propylene glycol as solvent in combination with mannitol 3%-12%, more preferably with mannitol 5%-10% w/v in water. Also, the use of propylene glycol as excipient in the present invention composition has a surprising advantage, because propylene glycol in a hyperosmotic concentration of 15% is known as an effective preservative (Rowe et al, loc. cit.).

Also concentrations below 15% propylene glycol (for instance 10%) are hyperosmotic and classified in the literature as having a preservative effect In the present invention composition this effect is enhanced by the presence of mannitol, making the total concentration of the ingredients of the nasal hydroxocobalamin composition hyperosmotic, resulting in a fully preserved nasal composition, with a consistent paracellular absorption of hydroxocobalamin and offering at the same time the possibility of avoiding the use of rather toxic preservatives such as benzalkonium chloride and benzyl alcohol.

In a further embodiment the invention provides also a nasal hydroxocobalamin solution administered as a nasal spray or drops or nasal gel using compositions without the use of any preservative. In this case the nasal hydroxocobalamin solution is manufactured in a sterile way and/or sterilized in the final stage of manufacturing and/or presented in a closed preservative free container to deliver a nasal spray or nasal drops or a nasal gel.

Also it may be possible, for instance when using larger volumes of the nasal hydroxocobalamin invention formulation. that a high concentration of propylene glycol in the nasal composition is less optimal. In such a case another embodiment of the present invention provides a nasal hydroxocobalamin solution administered as a nasal spray or drops or nasal gel, using compositions with the use of sorbic acid or potassium sorbate as a preservative. In experiments by Hofmann et al 2004 (Arch Otolaryngol Head Neck Surgery 2004; 130: 440-445) it has been proven that potassium sorbate, about 0.1% (w/w), is much more safe than benzalkonium chloride when used as a preservative in nasal products.

Sorbic acid and its salts, such as sodium sorbate, potassium sorbate, and calcium sorbate, are antimicrobial agents often used as preservatives. In general, the salts are preferred over the acid form because they are more soluble in water, but it is the acid form that is active (Wikipedia 2014, sorbic acid). The optimal pH for the antimicrobial activity is below pH 6.5. Sorbates are generally used at concentrations of 0.025% to 0.10%. As a consequence, the present invention offers in further embodiments a solution containing sorbic acid as preservative at a pH between 4 and 7 preferably below 6, more preferably between 4-6. Such a pH is also offering an optimal stability for the hydroxocobalamin because it is known from the literature that the pH of hydroxocobalamin injections on the market are made acidic. This acidic pH is obtained with special buffers or with acetic acid. For instance the injection Neo-B12 has a pH of 4.6 (www.medsafe.com). The invention formulation has also a pH between 4-7.

The present invention provides a composition for nasal administration comprising hydroxocobalamin in a dosage volume per nostril of 10-150 µl, preferably between 25-125 µl, more preferably 25 µl, 50 µl, 70 µl, 90 µl or 100 µl, and containing per dosage volume an amount of hydroxocobalamin between 10-1000 µg, preferably between 25-750 mg. more preferably 50 µg, 100 µg, 250, or 500 µg.

The consistent absorption of hydroxocobalamin from solutions containing a hyperosmotic concentrations of mannitol and propylene glycol in human volunteers is demonstrated in the experiments described below.

Experimental Section:

Healthy volunteers received a dose of 500 µg hydroxocobalamin in 50 µl nasal spray containing as main constituents hydroxocobalamin, mannitol 10% w/v, propylene glycol 10% v/v and water (total dose 500 µg hydroxocobalamin HCl) using an Aptar VP7 spray pump. The following increases of hydroxocobalamin blood levels (increase from C t=0 to Cmax after 30 minutes) were measured:
423, 598, 609, 562, 793, 478, 537, 389 pg/ml (=ng/l).
Mean increase per 500 µg Hydroxocobalamin: 549 pg/ml (SD=127 pg/ml=CV 23%)
Comparable results were obtained when using mannitol 5% w/v, propylene glycol 15% v/v and water.

None of the volunteers experienced irritation in the nose or the presence of red crustae in the nose afterwards. In none of the volunteers the vitamin B12 Cmax levels exceeded 1500 pg/ml. The mean increase in cobalamin level was 549 pg/ml, and the CV of 23% is far below 40%, indicating a very consistent absorption.

The results demonstrate that it is possible (1) to provide the patient with a nasal supplementation therapy of vitamin B 12, with a consistent absorption and without causing the unphysiologically high blood levels (not exceeding 2000 pg/ml or 1500 pg/ml), avoiding (2) the risk for acneiform dermatitis caused by the high blood levels after the injection therapy and (3) without the occurrence of red crustae in the nose and (4) avoiding the use of benzalkonium chloride and benzyl alcohol as preservatives

The invention claimed is:

1. A liquid aqueous pharmaceutical composition suitable for intranasal administration, the composition comprising hydroxocobalamin, and/or a pharmaceutically acceptable hydroxocobalamin salt, dissolved in a concentration above 0.1% (w/v) in water containing at least 3% mannitol (w/v) and less than 12% mannitol (w/v).

2. The liquid aqueous pharmaceutical composition according to claim 1, further comprising 3%, 4%, 5%, 6%, 7%, 8%, 9%, 10%, 11%, 12%, 13%, 14%, or 15% v/v propylene glycol as a solvent in combination with the mannitol in water.

3. The liquid aqueous pharmaceutical composition according to claim 1, further comprising a preservative chosen from potassium sorbate or sorbic acid or sorbic acid derivatives.

4. The liquid aqueous pharmaceutical composition according to claim 1, further comprising:
   one or more solvents selected from glycerol, polyethylene glycol, or alkoxypolyethylene glycol; and/or
   one or more excipients selected from buffers, antioxidants, agents to adjust the pH, surfactants, complexing agents, stabilizers, or solubilizers.

5. The liquid aqueous pharmaceutical composition according to claim 1, further comprising:
   3%, 4%, 5%, 6%, 7%, 8%, 9%, 10%, 11%, 12%, 13%, 14%, or 15% v/v propylene glycol as a solvent in combination with the mannitol in the water;

a preservative chosen from potassium sorbate or sorbic acid or sorbic acid derivatives;
one or more solvents selected from glycerol, polyethylene glycol, or alkoxypolyethylene glycol; and
one or more other excipients selected from buffers, antioxidants, agents to adjust the pH, surfactants, complexing agents, stabilizers, or solubilizers, wherein a total concentration of hydroxocobalamin in the liquid aqueous pharmaceutical composition is from 0.1% (w/v) to 2% (w/v).

* * * * *